United States Patent
Saito (10) Patent No.: US 8,449,515 B2
(45) Date of Patent: May 28, 2013

(54) PANTS-TYPE DISPOSABLE DIAPER COVER (75) Inventor: Tetsuhiro Saito, Sakura (JP)

(73) Assignee: Daio Paper Corporation, Ehime (JP)

( * ) Notice: Subject to any disclaimer, the term of this patent is extended or adjusted under 35 U.S.C. 154(b) by 797 days.

(21) Appl. No.: 12/087,131

(22) PCT Filed: Dec. 19, 2006

(86) PCT No.: PCT/JP2006/325287
§ 371 (c)(1),
(2), (4) Date: Jun. 25, 2008

(87) PCT Pub. No.: WO2007/074682
PCT Pub. Date: Jul. 5, 2007

(65) Prior Publication Data
US 2011/0144611 A1 Jun. 16, 2011

(30) Foreign Application Priority Data
Dec. 26, 2005 (JP) .................. 2005-372092

(51) Int. Cl.
*A61F 13/49* (2006.01)
*A61F 13/72* (2006.01)

(52) U.S. Cl.
USPC ............ 604/385.14; 604/385.22; 604/385.27; 604/385.3; 604/396

(58) Field of Classification Search
USPC .. 604/385.14, 385.16, 385.22, 385.24–385.3, 604/395–398
See application file for complete search history.

(56) References Cited

U.S. PATENT DOCUMENTS

| | | | | |
|---|---|---|---|---|
| 2,166,012 A | * | 7/1939 | La Maida | 604/394 |
| 6,169,225 B1 | * | 1/2001 | Otsubo | 604/361 |
| 6,530,091 B2 | * | 3/2003 | Takai et al. | 2/406 |
| 2002/0045872 A1 | * | 4/2002 | Shimada et al. | 604/385.3 |
| 2002/0143316 A1 | * | 10/2002 | Sherrod et al. | 604/385.101 |
| 2005/0131374 A1 | * | 6/2005 | Otsubo et al. | 604/385.27 |
| 2005/0267431 A1 | * | 12/2005 | Sasaki et al. | 604/385.3 |

FOREIGN PATENT DOCUMENTS

| | | | |
|---|---|---|---|
| JP | 5-62227 | | 8/1993 |
| JP | H05-62227 | * | 8/1993 |
| JP | 9-99006 | | 4/1997 |
| JP | 3058259 U | * | 10/1999 |
| JP | 2001-29375 | | 2/2001 |
| JP | 2003-24385 | | 1/2003 |
| JP | 2003-126148 | * | 7/2003 |
| JP | 2004-261332 | | 9/2004 |
| JP | 2005-270377 | | 10/2005 |

* cited by examiner

*Primary Examiner* — Lynne Anderson
*Assistant Examiner* — Kathryn E Ditmer
(74) *Attorney, Agent, or Firm* — Jordan and Hamburg LLP (57) ABSTRACT

Provided is a pants-type disposable diaper cover, which can mount an absorptive pad easily and which can hold the mounted absorptive pad snugly without any positional displacement. The pants-type disposable diaper cover has a structure, in which elastically extensible members are arranged between two nonwoven-fabric sheets, and in which a waist opening and a pair of right and left leg openings are formed. A pad-fixing sheet having its front end portion and back end portion fixed is arranged in a diaper cover region corresponding to the mounting portion of the absorptive pad. The diaper cover includes at least elastically extensible waist members arranged around the waist opening, and a plurality of curved elastically extensible members arranged to extend in a front and in a back from the body sides to the crotch side, to cross the arranged portions of the absorptive pad on the crotch side, and then to draw a plurality of loci extending from the crotch side to the body sides.

5 Claims, 8 Drawing Sheets

(A) (EXTENDED STATE)

(B) (PRODUCT STATE)

PANTS-TYPE DISPOSABLE DIAPER COVER

BACKGROUND OF THE INVENTION

The present invention relates to a pants-type disposable diaper cover having a renewable type absorptive pad made removable.

In the prior art, the disposable diaper is divided into the tape- or pants-type paper diaper, which is integrated with an absorbent so that it is discarded after a bodily liquid is absorbed one or several times, and the so-called "diaper cover type", in which a renewable absorptive pad is made removable. The latter diaper cover type is advantageous in that the diaper cost can be lowered by renewing inexpensive absorptive pads.

In the diaper cover, generally speaking, a male fastener is attached to the back side of an absorptive pad in order to fix the absorptive pad on the diaper cover so as not to displace the pad in wearing. On the other hand, a female fastener is attached to the inner face of the diaper cover so as to fix the absorptive pad. The absorptive pad is fixed for use on the diaper cover by bringing the face fastener of the absorptive pad and the face fastener of the shorts into engagement in a facing relationship.

In recent years, moreover, there are proposed a variety of diaper covers which are intended to improve the wearing feel. In the following Patent Document 1, for example, there are proposed shorts (or a diaper cover), which are put on together with an absorptive pad having a face fastener with a male member, which is extensible at least vertically and in which a smooth region not engaged with the male member of the absorptive pad is formed on the inner faces at the front and/or the back.

In the following Patent Document 2, moreover, there is proposed a diaper, which is put on to cover the crotch of a human body and the abdominal region and the buttocks positioned in front of and at the back of the crotch, thereby to receive the excrement due to an incontinence. The diaper comprises: an absorptive pad including an absorbent for receiving the excrement due to the incontinence, and having a shape for contacting sufficiently with the crotch of the human body and the abdominal region and the buttocks positioned in front of and at the back of the crotch and a water absorbing ability to absorb an average quantity of the excrement composed mainly of the urine due to the incontinence; and a holder (or a diaper cover) made separate of the above absorptive pad and holding the absorptive pad in a manner to wrap the absorptive pad entirely and the human body therearound. The absorptive pad includes a crotch abutting portion having a width corresponding to the crotch of the human body, a wide front abutment portion corresponding to the abdomen positioned in front of the crotch of the human body, and a wide back abutment portion corresponding to the buttocks positioned at the back of the crotch of the human body. Moreover, the holder includes a body formed of a three-dimensionally extensible material for wrapping the absorptive pad entirety and the human body therearound, a crotch portion positioned below the crotch of the human body, and leg passing portions for passing the legs of the human body.

Patent Document 1: JP-A-2003-24385
Patent Document 2: JP-A-2001-29375

SUMMARY OF THE INVENTION

First of all, however, most of the diaper covers thus far provided in the prior art employs a single material, a blended material, a knitted material or a woven material of cotton, nylon, polyurethane, and polynosic as described in the Patent Documents 1 and 2. Therefore, the diaper covers are troubled by a problem that the production cost is high.

On the other hand, the diaper cover is poor in the wearing operation of the absorptive pad and cannot prevent the positional displacement completely because it resorts to only mechanical joining means such as the face fastener. When the diaper cover is put off for re-wearing it or in a toilet, moreover, the absorptive pad and the diaper cover mismatch each other in their extensions, thus causing a problem that the face fasteners fixing the absorptive pad go out of engagement.

Therefore, a main object of the invention is to provide a pants-type disposable diaper cover, which can be manufactured at a low cost, which can mount an absorptive pad easily, which can hold the mounted absorptive pad snugly without any positional displacement, and which can be prevented from having the absorptive pad disengaged when the diaper cover is put on again or when the wearer does his or her needs at a toilet.

In order to solve the aforementioned problems, according to a first aspect of the invention, there is provided a pants-type disposable diaper cover having a renewable type absorptive pad made removable, wherein the pants-type disposable diaper cover is constituted such that elastically extensible members are arranged between two nonwoven-fabric sheets, and such that a waist opening and a pair of right and left leg openings are formed when the diaper cover is folded at a diaper crotch portion and when a front and a back are joined at two side portions, characterized:

in that a pad-fixing sheet having at least its front end portion and back end portion fixed is arranged in a diaper cover region corresponding to the mounting portion of the absorptive pad; and in that the diaper cover includes at least elastically extensible waist members arranged around the waist opening, and a plurality of curved elastically extensible members arranged to extend in a front and in a back from the body sides to the crotch side, to cross the arranged portions of the absorptive pad on the crotch side, and then to draw a plurality of loci extending from the crotch side to the body sides.

In the first aspect of the invention, the diaper cover itself is constituted of a sheet material, in which the elastically extensible members are arranged between the two nonwoven-fabric sheets, so that the manufacturing cost can be low. Moreover, the pad-fixing sheet having at least its front end portion and back end portion fixed is arranged in the diaper cover region corresponding to the mounting portion of the absorptive pad. As will be described hereinafter, therefore, it is possible to improve the wearing efficiency of the absorptive pad, and the wearing feel, the close touch and the followability of the absorptive pad, and to prevent the absorptive pad from being disengaged for re-wearing the diaper cover or for doing his or her needs.

Moreover, the elastically extensible members arranged in the diaper cover are constituted so as to include at least the elastically extensible waist members arranged around the waist opening, and the curved elastically extensible members arranged to extend in a front and in a back from the body sides to the crotch side, to cross the arranged portions of the absorptive pad on the crotch side, and then to draw a plurality of loci extending from the crotch side to the body sides. Especially the latter curved elastically extensible members form the extensible zones to touch the body closely on the side portions of the mounted portion of the absorptive pad so that the absorptive pad mounted can be snugly held without any positional displacement.

According to a second aspect of the invention, there is provided a pants-type disposable diaper cover of the first aspect of the invention, wherein the absorptive pad is joined to the pad-fixing sheet by either a self-adhesive applied to the back of the absorptive pad or face fasteners disposed on the absorptive pad and the pad-fixing sheet.

According to a third aspect of the invention, there is provided a pants-type disposable diaper cover according to the first or second aspect of the invention, further including a plurality of elastically extensible hip members arranged in the front and back at a vertical spacing along a horizontal direction.

In the third aspect of the invention, for the diaper cover, not only the elastically extensible waist members and the curved elastically extensible members but also the elastically extensible hip members are provided so that a fitness can be given to the hip portion.

According to a fourth aspect of the invention, there is provided a pants-type disposable diaper cover according to any of the first to third aspects of the invention, wherein the curved elastically extensible members are arranged through a spacing without intersecting each other.

In the fourth aspect of the invention, the curved elastically extensible members are arranged through the spacing without intersecting each other so that the elastic forces are not concentrated but homogeneously balanced so that the whole diaper cover can be made to touch the body closely.

According to a fifth aspect of the invention, there is provided a pants-type disposable diaper cover according to any of the first to fourth aspects of the invention, wherein the curved elastically extensible members arranged in said front and back cross in the transverse portion of the crotch side either substantially straight along the transverse direction or in arcuate curve shapes bulging to the crotch side.

The absorptive pad can be held in close touch on the body side by the pushing forces of the curved elastically extensible members crossing the crotch side.

According to a sixth aspect of the invention, there is provided a pants-type disposable diaper cover according to any of the first to fifth aspects of the invention, wherein the curved elastically extensible members arranged in the back are directionally turned back in the crossing portion on the crotch side to the sides of the waist opening to draw a locus building to the sides of the waist opening at the substantially widthwise center and are then so turned back again that they cross in a locus of the shape of letter W substantially as a whole.

The convex locus portion, as positioned at the center of the diaper cover, is deformed along the recess of the buttocks thereby to push the absorptive pad to the body side so that the structure can establish no clearance with the recess of the buttocks.

According to a seventh aspect of the invention, there is provided a pants-type disposable diaper cover according to any of the first to sixth aspects of the invention, wherein the starting and terminating ends of the curved elastically extensible members are any or a combination of the joining edges to join the front and the back, the waist opening edge and the leg opening edges.

According to the invention, as has been described in detail, it is possible to provide the pants-type disposable diaper cover, which can be manufactured at a low cost, which can mount the absorptive pad easily, which can hold the mounted absorptive pad snugly without any positional displacement, and which can be prevented from having the absorptive pad disengaged when the diaper cover is put on again or when the wearer does his or her needs at a toilet.

DETAILED DESCRIPTION OF THE INVENTION

In the following, modes of embodiment of the invention are described in detail with reference to the accompanying drawings.

Figure 1:
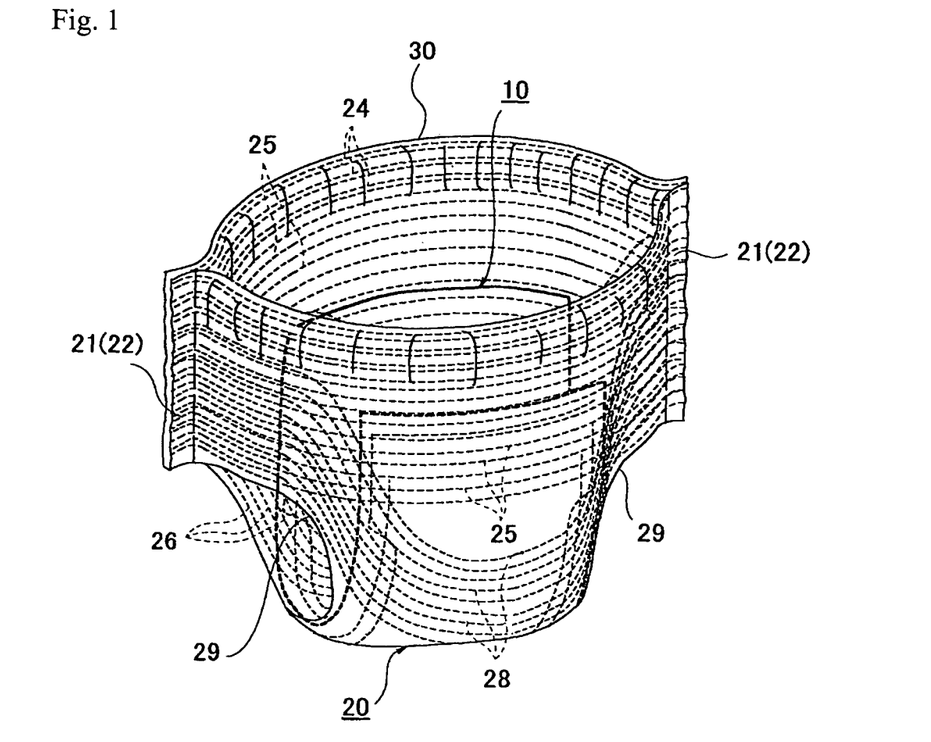
FIG. 1 is a perspective view showing the state, in which an absorptive pad 10 is mounted on a pants-type disposable diaper cover 20 according to the invention.
Figure 2:
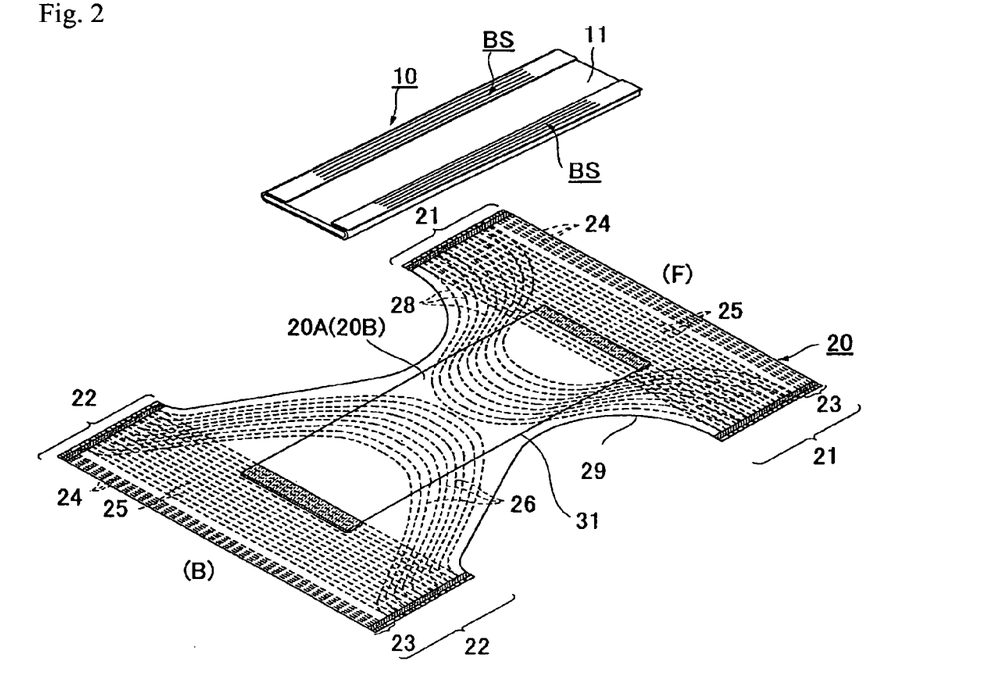
FIG. 2 is a perspective view of the extended state of the same.
Figure 3:
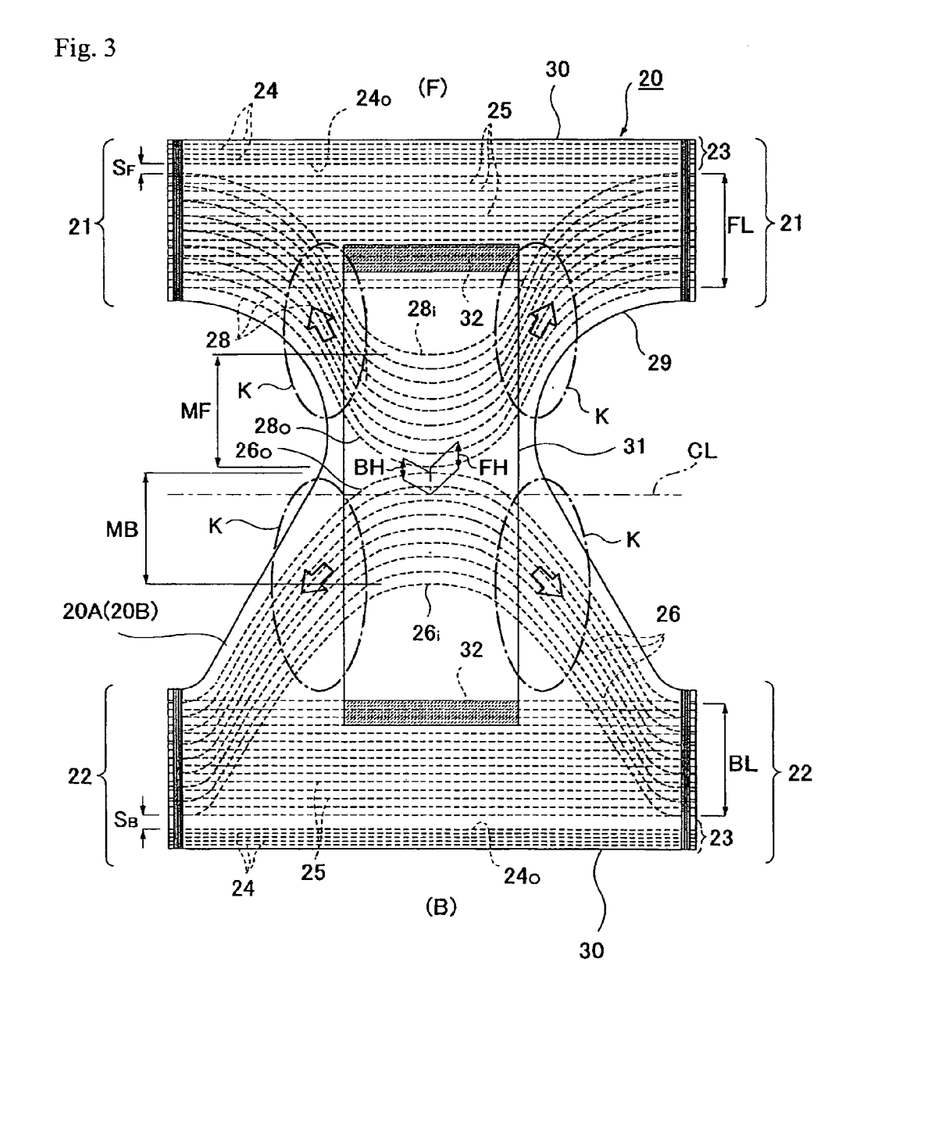
FIG. 3 is an extended development of the diaper cover 20.
Figure 4:
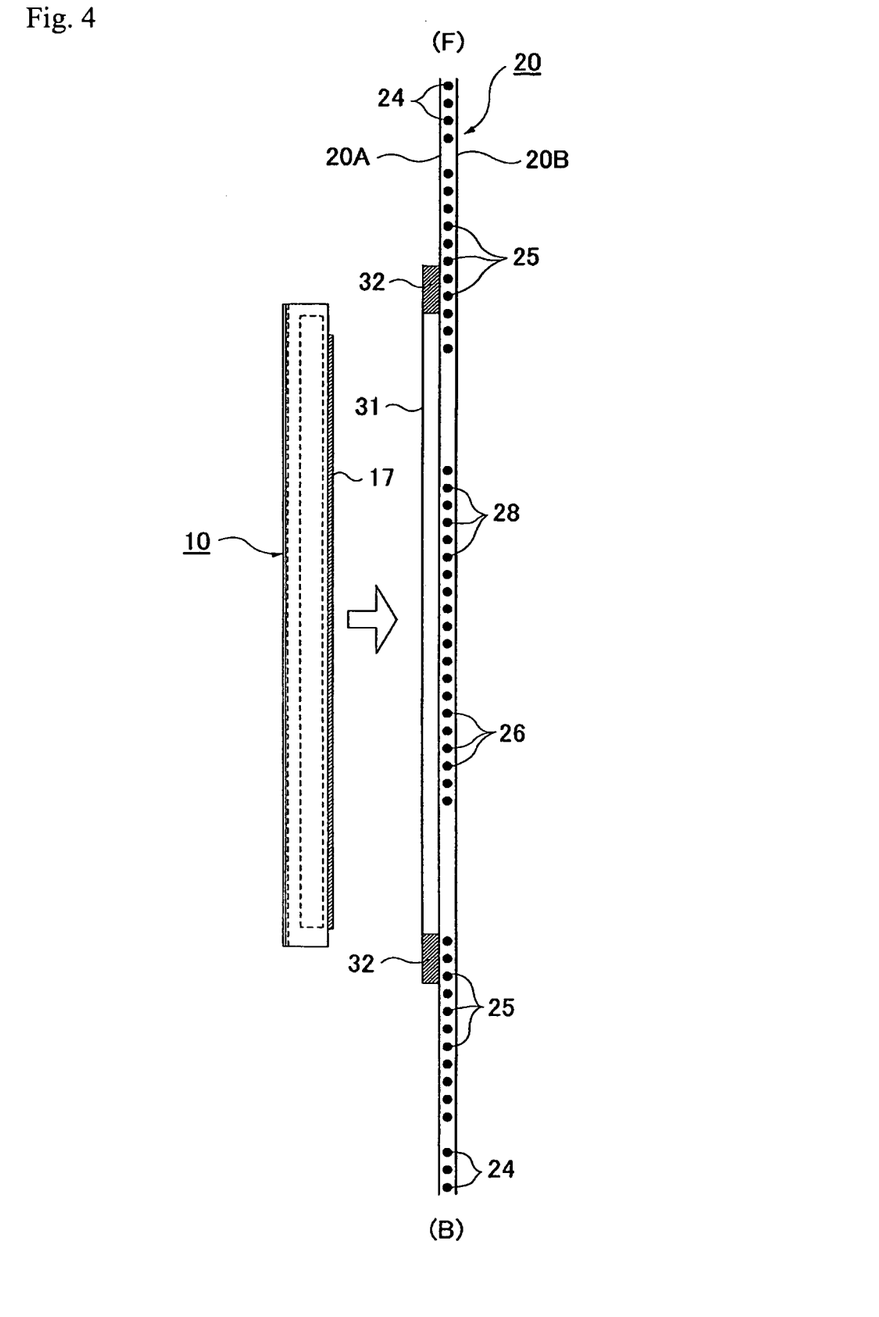
FIG. 4 is a longitudinal section of the diaper cover 20.

FIG. 1 is a perspective view showing the state, in which an absorptive pad 10 is mounted on a pants-type disposable diaper cover 20 according to the invention; FIG. 2 is a perspective view of the extended state of the same; and FIG. 3 is an extended development of the diaper cover 20.

As shown in FIG. 1 and FIG. 2, the present pants-type disposable diaper cover 20 (as will be called the "diaper cover") has the replaceable absorptive pad 10 made removable on the inner side. A variety of elastically extensible members are arranged between two nonwoven fabric sheets 20A and 20B. The diaper cover 20 is folded at a diaper crotch portion, and a front F and a back B are joined on the two side portions. As a result, the diaper cover 20 is given a structure, in which a waist opening 30 and a pair of right and left leg openings 29 and 29 are formed.

In the following, the absorptive pad 10 and the diaper cover 20 are described sequentially in the recited order.

(Structure of Absorptive Pad 10)

Figure 5:
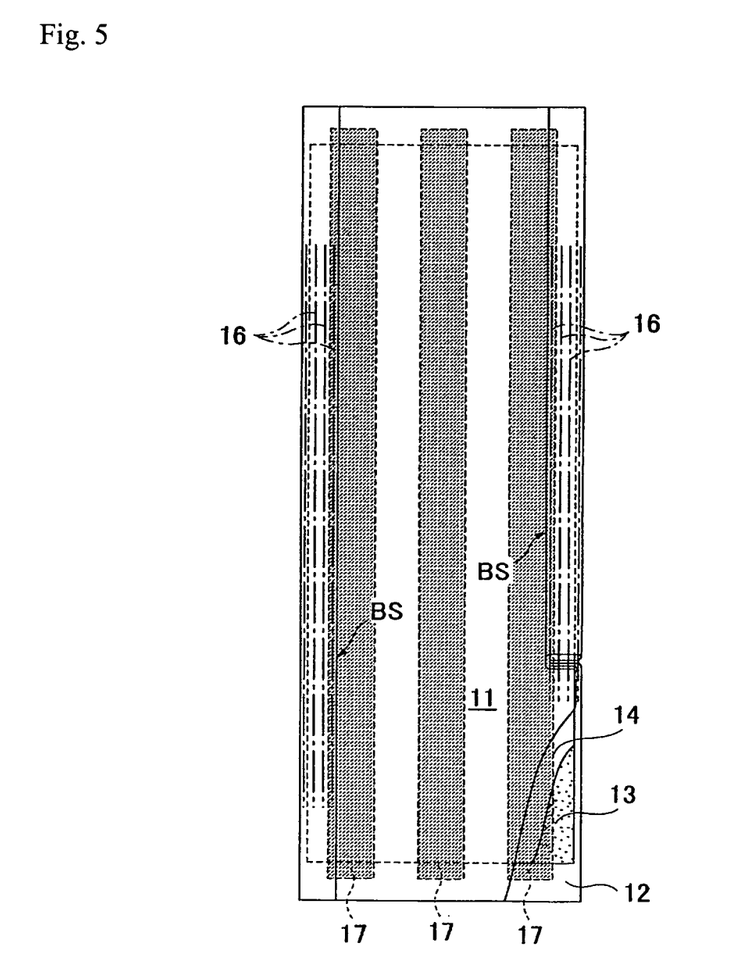
FIG. 5 is a top plan view of the absorptive pad 10.

First of all, one example of the structure of the absorptive pad 10 is described in detail with reference to FIG. 5 and FIG. 6.

The absorptive pad 10 is given a structure, in which an absorbent 13 of cotton-like pulp is interposed between a liquid-permeable surface sheet 11 made of nonwoven fabric or the like and a leakage-preventing sheet 12 made of polyethylene or the like, thereby to absorb and hold a bodily liquid.

The absorbent 13 used in the shown embodiment is shaped to have a substantially rectangular top plan shape, the width size of which gives no stiffness to the wearer by the abutment against the crotch portion. This absorbent 13 is enclosed by crepe paper 14 so as to hold the shape and to improve the diffusibility of the bodily liquid having passed the liquid-permeable surface sheet 11. Here, it is desired to exemplify the absorbent 13 by an air-laid absorbent capable of minimizing the bulk.

The liquid-permeable surface sheet 11 for covering the surface side (or the surface touching side) of the absorbent 13 is preferably exemplified by porous or non-porous nonwoven fabric or a porous plastic sheet. The material fibers for constituting the nonwoven fabric can be exemplified by synthetic fibers of an olefin group such as polyethylene or polypropylene, a polyester group or a polyamide group, reproduced fibers such as rayon or cupra, or natural fibers such as cotton, and the nonwoven fabric can be prepared by a suitable working method such as a spun-lace method, a spun-bond method, a thermal-bond method, a melt-blown method or a needle-punch method. Of these working methods, the spun-lace method is excellent in rich flexibility and drapability, and the thermal-bond method is excellent in bulkiness and softness. The liquid-permeable surface sheet 11 absorbs urine or the like quickly, in case it has multiple pores formed therein, so that it is excellent in dry touch. The liquid-permeable surface sheet 11 extends to the back side of the absorbent 13 while wrapping the side edge portions of the absorbent 13.

The leakage-preventing sheet 12 used to cover the back side (or the side not to abut against the skin) of the absorbent 13 is made of a liquid-impermeable plastic sheet such as polyethylene or polypropylene. In recent years, however, the leakage-preventing sheet 12 preferably used is moisture-permeable from the standpoint of preventing the stuffiness. The water-impermeable/moisture-permeable sheet is exemplified by a fine multi-porous sheet, which is prepared, for example, by melting and kneading an inorganic filler into an olefin resin such as polyethylene or polypropylene to form a sheet and then by extending the sheet in one or two axial directions. This sheet has a lower rigidity than the non-porous sheet for an equal sheet thickness so that it is superior in the point of softness.

Figure 6:
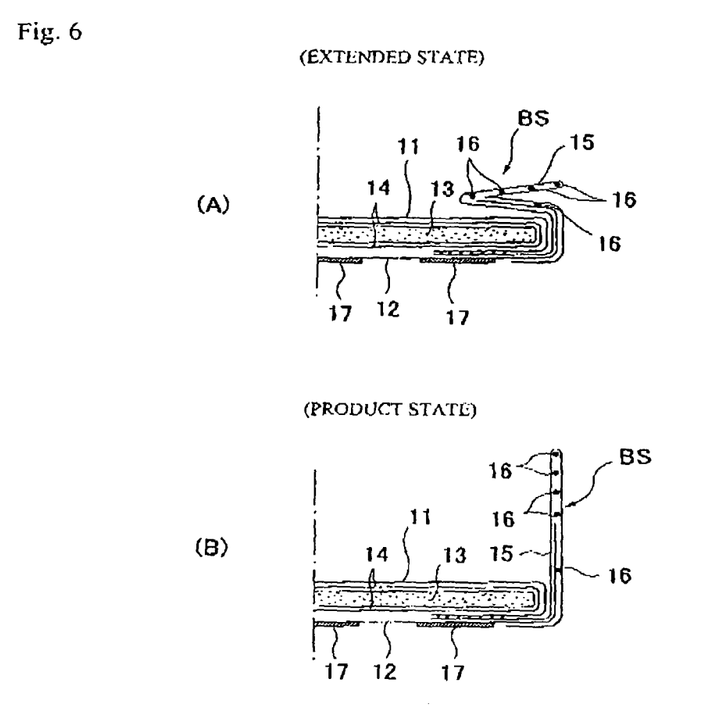
FIG. 6A is a transverse section of one half of the absorptive pad 10 in an extended state.
FIG. 6B is a transverse section of one half of the same in a product state (or in a put-on state).

On the other hand, a gathered non-woven fabric 15 forming stereo gathers BS is made of a double sheet by folding it back, as shown in FIG. 6, and is extended and adhered to the back side of the absorbent 13, as wrapped by the liquid-permeable surface sheet 11, while wrapping the side edge portions of the absorbent 13 from the upper sides. More specifically, the gathered non-woven fabric 15 is adhered, at the longitudinally intermediate portion of the diaper cover 20, by means of a hot-melt adhesive over the range from the widthwise intermediate portion to the back side of the absorbent 13 while leaving the portions forming the stereo gathers BS. Moreover, the gathered non-woven fabric 15 is adhered, at the longitudinally front and back end portions, by means of a hot-melt adhesive over the range from widthwise intermediate portion to one side end edge and over the back side of the absorbent 13 while folding the portions to form the stereo gathers BS on the upper face of the absorbent 13.

Inside of the gathered non-woven fabric 15 formed of the double-sheet nonwoven fabric, a plurality of elastically extensible thread members 16 are arranged at the rising leading-end side portions. These elastically extensible thread members 16 are raised in a product state (conveying a state of wear by a user) by the elastically extensible force, as shown in FIG. 6(B), at the non-woven fabric portions protruding from the absorbent-side edge portions, thereby to form the stereo gathers BS.

The leakage-preventing sheet 12 proceeds so far as to go into the inside of the gathered non-woven fabric 15 of the double-sheet shape thereby to constitute leakage-preventing walls on the lower-end sides of the stereo gathers BS, as shown in FIG. 6. This leakage-preventing sheet 12 used is desirably made opaque so that it may shield the brown color of stool or urine. An opaque film to be properly used is prepared by adding into plastics a pigment or filler such as calcium carbonate, titanium oxide, zinc oxide, white carbon, clay, talc or barium sulfate.

The elastically extensible thread members 16 can be made of a normally used material such as styrene group rubber, olefin group rubber, urethane group rubber, ester group rubber, polyurethane, polyethylene, polystyrene, styrene butadiene, silicon or polyester. The elastically extensible thread members 16 may be made to have a thickness of 925 dtex or less and a tension of 150 to 350% and arranged at an interval of 7.0 mm or less, so that they may be hard to see from the outside. Here, the elastically extensible thread members may also be replaced by an elastically extensible tape member.

The material fibers constituting the gathered non-woven fabric 15 can also be exemplified, as in the liquid-permeable surface sheet 11, by the synthetic fibers of the olefin group such as polyethylene or polypropylene, the polyester group or the amide group, the reproduced fibers such as rayon or cupra, or the natural fibers such as cotton, and the nonwoven fabric can be prepared by the suitable working method such as the spun-bond method, the thermal-bond method, the melt-blown method or the needle-punch method. In order to prevent the stuffiness especially, it is advisable to use the non-woven fabric which is made excellent in air-permeability by suppressing the basis weight. In order to prevent permeation of the urine and to prevent a rash thereby to enhance the skin feel (or the dry feel), moreover, the gathered non-woven fabric 15 is desirably made of the nonwoven fabric which is made water-repellent by coating it with a water-repelling agent such as a silicone group, a paraffin-metal group or an alkylchromic chloride group.

The absorptive pad 10 is coated on the back side with peelable self-adhesive layers 17, and is removably mounted on a pad-fixing sheet 31 of the later-described diaper cover 20.

(Structure of Diaper Cover 20)

As shown in FIG. 2 and FIG. 3, the diaper cover 20 is made into a nonwoven fabric sheet having a two-layer structure composed of the upper layer nonwoven fabric sheet 20A and the lower layer nonwoven fabric sheet 20B, between which various elastically extensible members are arranged so that the nonwoven-fabric sheets are extensible. The top plan shape is generally formed into an hourglass shape by the recessed leg cut lines 29 (or the leg openings) formed to form the leg openings in the two intermediate side portions.

The diaper cover 20 is equipped with the pad-fixing sheet for mounting the absorptive pad 10 on its region corresponding to the mounting portion of the absorptive pad 10, such that at least the front end portion and the back end portion may not peel with adhesives 32 and 32. The pad-fixing sheet 31 can be made of an arbitrary sheet material such as woven fabric, nonwoven fabric or a plastic film. It is preferred to use an air-permeable material. Here, the pad-fixing sheet 31 is desirably fixed only at two portions, i.e., at the front end portion and the back end portion so as to raise no obstruction to the extensibility of the diaper cover 20 and to improve the followability to the body motion. As the case may be, however, the pad-fixing sheet 31 may also be fixed at the intermediate portion.

The pad-fixing sheet 31 improves not only the wearing efficiency of the absorptive pad but also the wearing feel, the close touch and the followability of the absorptive pad 10. Specifically, the pad-fixing sheet 31 can give a mark, when the absorptive pad 10 is mounted on the diaper cover 20, so that the absorptive pad 10 can always be mounted at the same position. Moreover, the diaper cover 20 has so many small wrinkles formed by the various elastically extensible members that it is troubled by the problem that its adhesion is made difficult and weakened. By providing the pad-fixing sheet 31 separately, however, the joining face to be adhered to the absorption pad 10 can be flattened to adhere the absorptive pad 10 reliably and firmly. Even if the diaper cover 20 is extended at the wearing time, moreover, the pad-fixing sheet 31 intervenes so that the extending force does not act directly so that the adhesion is not broken even when the diaper cover is put off for re-wearing or for doing his or her needs.

In the put-on state, moreover, the pad-fixing sheet 31 intervenes to remove various elastically extensible members 26 and 28, and the diaper cover 20 can extend and contract freely according to the body shape or the body motions, thereby to improve the wearing feel, the close touch and the followability to the body motions.

At each time of changing the absorptive pad 10, the adhesion and the peel are repeated. If the absorptive pad 10 is adhered not through the pad-fixing sheet 31 but directly on to the diaper cover 20, the nonwoven-fabric sheet 20A may be torn. However, this problem of breakage can be solved in case the absorptive pad 10 is adhered to the pad-fixing sheet 31.

On the other hand, the elastically extensible members to be arranged in the diaper cover 20 are, in the expanded shape shown in FIG. 3, and elastically extensible waist members 24 arranged in a waist opening periphery 23; a plurality of elastically extensible hip members 25 arranged at the front F and the back B horizontally and at a vertical spacing with respect to one another. In addition to the elastically extensible hip members 25, individually at the front F and the back B, moreover, there are the curved elastically extensible members 26 and 28, which extend from the one side joining edges for joining the front F and the back B to the crotch side, and which cross the arranged portions of the absorptive pad 10 on the crotch side and reach the other side joining edges of the front and the back from the crotch side. Of these elastically extensible members, at least the elastically extensible waist members 24 and the curved elastically extensible members 26 and 28 are desirably provided.

In the following, the various elastically extensible members are individually described in detail.

The elastically extensible waist members 24 are a plurality of elastically extensible rubber thread members arranged at a vertical spacing near the waist opening edge in side-joining edges 21 and 22 where the front F and the back B are joined. The elastically extensible waist members 24 apply elastically extending forces to fasten the waist portion of the body thereby to put the diaper cover 20 on the body. These elastically extensible waist members 24 are made of the rubber threads in the shown example but may also be made of tape-shaped elastically extensible members.

The elastically extensible hip members 25 are a plurality of elastically extensible rubber thread members arranged horizontally at a vertical spacing in the side-joining edges 21 and 22 over a range generally from the upper portion to the lower portion. The elastically extensible hip members 25 apply horizontally elastically extending forces to the hip portions of the front F and the back F thereby to hold the diaper cover 20 in close touch with the body. Here, the boundaries between the elastically extensible waist members 24 and the elastically extensible hip members 25 need not always be clear. Of the elastically extensible members arranged horizontally at a vertical spacing in the front F and the back B, for example, some of the upper side may act as the elastically extensible waist members, although their number cannot be specified, and the remaining elastically extensible members may function as the elastically extensible hip members.

In the front of the diaper cover 20, on the other hand, the curved elastically extensible back members 26, as arranged separately of the elastically extensible hip members 25, are a plurality or nine in the shown example of elastically extensible rubber thread members arranged to extend from the side-joining edges 22 on one side to the crotch portion substantially along the leg cut lines 29, to cross the arranging portion of the absorptive pad 10 on the crotch side and to reach the side-joining edges 22 on the other side substantially along the leg cut lines 29 on the opposite side. Five or more, preferably seven or more curved elastically extensible back members 26 are so arranged at a predetermined spacing as to form predetermined elastically extensible zones K at buttocks.

The starting ends of the curved elastically extensible back members 26 are connected at a predetermined spacing over ranges from the upper portions to the lower portions of the joining edges of the front F and the back B. In the side-joining edges 21 and 22 between the front F and the back B, that elastically extensible member $26_i$ of the curved elastically extensible back members 26, which is positioned the closest to the waist opening, is desirably arranged such that a distance $S_B$ from the lowermost elastically extensible member $24_0$ of the elastically extensible waist members 24 is within 20 mm. When the wearer grips and pulls up the sides of the waist portion so as to wear the diaper cover 20, the wearer can pull up the side of the back B of the diaper cover 20 easily with the elastic forces of the curved elastically extensible back members 26 so that the wearing easiness is improved.

Moreover, the curved elastically extensible back members 26 are desired to cross in the crossing portion on the crotch side either substantially straight in the transverse direction or in the arcuately curved shape bulging to the crotch side, as shown.

In the diaper cover 20, at the back B, in order to fit the diaper cover 20 to the bulging shape of the buttocks, the elastically extensible members 26 are so arranged at relatively gentle inclination angles as to act the extending forces as much as possible along the bulging buttocks. Thus, the diaper cover 20 can wrap the body in a close touch to envelop the buttocks.

Moreover, the arranging interval between the curved elastically extensible back members 26 in the side-joining edges 21 and 22 of the front F and the back B, that is, the arranging interval in the arranging section BL of the elastically extensible members of the side-joining edges 21 and 22 are made substantially equal to the arranging interval of the curved elastically extensible back members 26 in the arranging section MB of the elastically extensible members of the crotch portion. At the same time, of the curved elastically extensible back members 26, that elastically extensible member $26_0$, which is positioned the closest to the crotch side, is arranged to draw such a curve that the distance BH from a crotch folding line CL of the diaper may be within ±50 mm, preferably within 35 mm. The arranging interval of the curved elastically extensible back members 26 is equalized between the side-joining edges 21 and 22 and at the crotch portion, so that the elastic force is not concentrated to make the diaper cover 20 in close touch with the body in a homogeneous balance. At the same time, the lines drawn by the curved elastically extensible back members 26 are arranged in a curved shape of large waves to cross the region near the crotch portion, so that the diaper cover 20 can be held in close touch with the body.

The curved elastically extensible back members 26 arranged on the side of the back B are desirably biased in the crotch portion to the side of the front F with reference to the crotch portion folding line CL of the diaper. In the crotch portion, the curved elastically extensible back members 26 are biased to the side of the front F with reference to the crotch portion folding line CL of the diaper so that the diaper can be prevented from slipping down on the side of the buttocks and so that the diaper cover 20 can be made so tight as to fit the body.

In the front of the diaper cover 20, on the other hand, the curved elastically extensible abdomen members 28, as arranged separately of the elastically extensible hip members 25, are a plurality or nine in the shown example of elastically extensible rubber thread members so arranged at a spacing without intersection as to extend from the side-joining edges 21 on one side to the crotch portion, to cross the arranging portion of the absorptive pad on the crotch side and to reach the side-joining edges 21 on the other side. Those curved elastically extensible abdomen members 28 are arranged at a spacing without any intersection. Five or more, preferably seven or more curved elastically extensible abdomen members 28 are so arranged at a predetermined spacing as to form the predetermined elastically extensible zones K at the inguinal region.

The starting ends of the curved elastically extensible abdomen members 28 are connected at a predetermined spacing over ranges from the upper portions to the lower portions of the joining edges 21 of the front F and the back B. In the side-joining edges 21 and 22 between the front F and the back B, that elastically extensible member $28_i$ of the curved elastically extensible abdomen members 28, which is positioned the closest to the waist opening, is desirably arranged such that a distance $S_F$ from the lowermost elastically extensible member $24_0$ of the elastically extensible waist members is within 20 mm. When the wearer grips and pulls up the sides of the waist portion so as to wear the diaper cover 20, the wearer can pull up the side of the front F of the diaper cover 20 easily with the elastic forces of the curved elastically extensible abdomen members 28 so that the wearing easiness is improved.

The curved elastically extensible abdomen members 28 are also desired to cross in the crossing portion on the crotch side either substantially straight in the transverse direction or in the arcuately curved shape bulging to the crotch side, as shown.

The present diaper cover 20 does not have such a bulging portion on the front-side portion of the body as is formed on the buttock portion on the back side of the body. In view of the finding that the slip-down of the diaper cover 20 prominently occurs mainly on the side of the front F, therefore, the elastically extensible members 28 are arranged at relatively steep angles of inclination thereby to prevent the diaper cover 20 effectively from slipping down.

Moreover, the arranging interval between the curved elastically extensible abdomen members 28 in the side-joining edges 21 and 22 of the front F and the back B, that is, the arranging interval in the arranging section FL of the elastically extensible members of the side-joining edges 21 and 22 are made substantially equal to the arranging interval of the curved elastically extensible abdomen members 28 in an arranging section MF of the elastically extensible members of the crotch portion. At the same time, of the curved elastically extensible abdomen members 28, that elastically extensible member $28_0$, which is positioned the closest to the crotch side, is arranged to draw such a curve that a distance FH from the crotch folding line CL of the diaper may be within ±150 mm, preferably within 35 mm. The arranging interval of the curved elastically extensible abdomen members 28 is equalized between the side-joining edges 21 and 22 and at the crotch portion, so that the elastic force is not concentrated to make the diaper cover 20 in close touch with the body in a homogeneous balance. At the same time, the lines drawn by the curved elastically extensible abdomen members 28 are arranged in a curved shape of large waves to cross the region near the crotch portion, so that the diaper cover 20 can be held in close touch with the body.

The elastically extensible member $28_0$ the closest to the crotch portion of the curved elastically extensible abdomen members 28 arranged on the front F and the elastically extensible member $26_0$ the closest to the crotch portion of the curved elastically extensible back members 26 arranged on the back B are desired not to intersect each other in the crotch portion but to be close to each other. It is desired that the closest width (FH-BH) is 10 to 20 mm. In the crotch portion, the absorptive pad 10 is pushed under a homogeneous pressure to touch closely with the body side by the curved elastically extensible members 28 and 26 so that the clearance from the body is sealed to exhibit a high leakage-preventing effect.

(Other Modes of Embodiment)

(1) In the aforementioned mode example, the absorptive pad 10 is adhered to the pad-fixing sheet 31 by applying the self-adhesive layers 17 to the back side thereof. By providing the absorptive pad 10 with planar male or female fasteners on its back side and by providing the pad-fixing sheet 31 with the planar female or male fasteners on its upper face, however, the absorptive pad 10 may also be joined to the pad-fixing sheet 31. Alternatively, the absorptive pad 10 is provided with flaps extending from the side edges to the outside, and self-adhesive layers are formed on the back sides of the flaps. Just like the well-known napkin with wings, the absorptive pad 10 is joined to the upper face of the pad-fixing sheet 31, and the flaps are then adhered around to the back side of the pad-fixing sheet 31.

Figure 7:
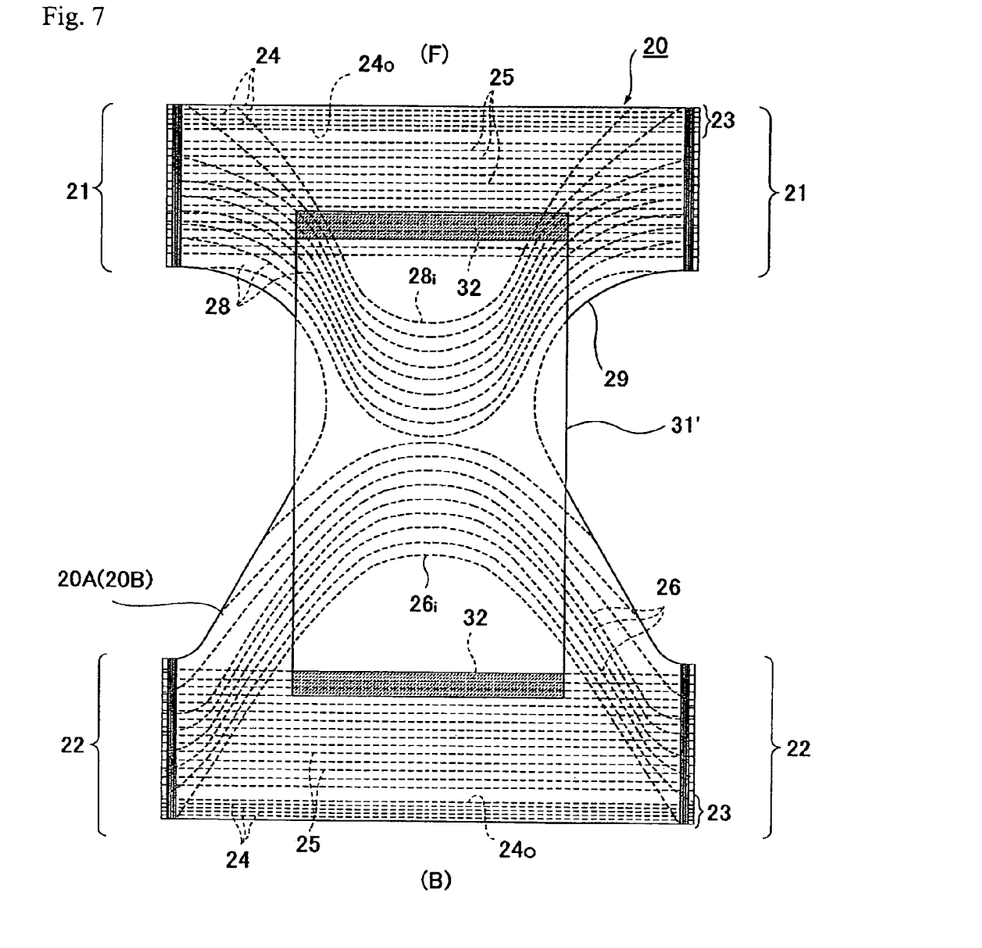
FIG. 7 is an extended development of the diaper cover 20 showing modifications of the arranging modes of the curved elastically extensible members 26 and 28 and modifications of a pad-fixing sheet 31.

(2) In the aforementioned mode example, the width size of the pad-fixing sheet 31 is made smaller than that of the crotch portion of the diaper cover 20. As shown in FIG. 7, however, a pad-fixing sheet 31' may have a width size larger than that of the crotch portion of the diaper cover 20.

Figure 8:
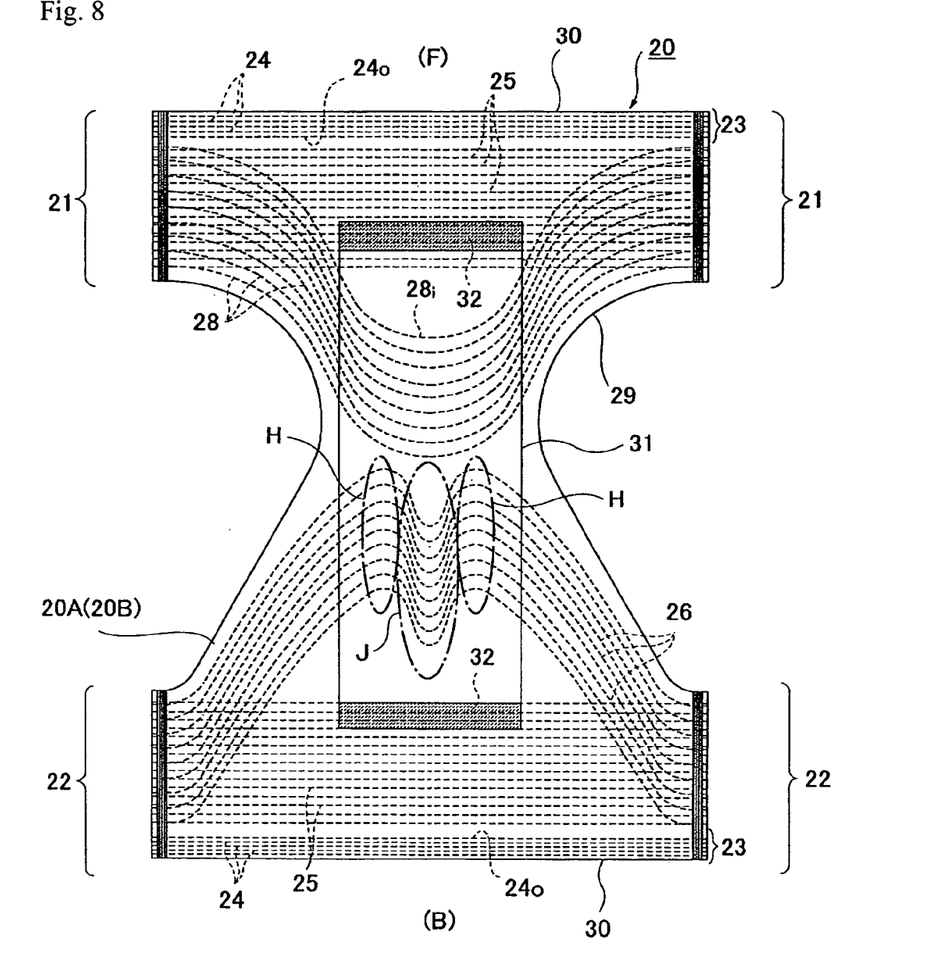
FIG. 8 is an extended top plan view of the diaper cover 20 showing another arranging mode of the elastically extensible back members 26.

(3) In the aforementioned mode example, the curved elastically extensible back members 26 are made to cross in the crossing portion on the crotch side either in the substantially straight shape along the transverse direction or in the arcuately curved shape bulging to the crotch side. As shown in FIG. 8, however, the curved elastically extensible back members 26 are turned back to the side of the waist opening 30 to draw a locus bulging to the sides of the waist opening 30, and are then so turned back again that they cross in a locus of the shape of letter W substantially as a whole. In this case, the recessed locus portions (or the convex locus portions toward the crotch side) H and H, which exist on the two sides of a convex locus portion J positioned at the center of the diaper cover 20, are desired to correspond to the buttocks, respectively. By causing the curved elastically extensible back members 26 along the substantially W-shaped locus, the convex locus portion J, as positioned at the center of the diaper cover 20, is deformed along the recess of the buttocks thereby to push the absorptive pad 10 to the body side. Thus, this structure establishes no clearance with the recess of the buttocks.

(4) In the aforementioned mode example, the curved elastically extensible members 26 and 28 start and terminate at the side-joining edges 21 and 22. However, the starting and terminating ends need not be limited to the joining edges of the front and the back but may be positioned at the waist opening edge or the leg opening edges. The "body side" in the invention has a concept containing the joining edges joining the front and the back, the side (as referred to FIG. 7) of the waist opening edge, and the sides of the leg opening edges. The curved elastically extensible members 26 and 28 may be arranged to draw a locus having a locus portion from those body sides to the crotch side, a locus portion crossing the arranging portion of the absorptive pad on the crotch side, and a locus portion extending from the crotch side to the body sides.

(5) In the aforementioned mode example, the elastically extensible member $28_0$ the closest to the crotch portion of the curved elastically extensible abdomen members 28 arranged on the front F and the elastically extensible member $26_0$ the closest to the crotch portion of the curved elastically extensible back members 26 arranged on the back B are disposed close to each other without intersecting each other in the crotch portion. However, the portions of the curved elastically extensible back members 26 and the portions of the curved elastically extensible back members 26 may also intersect each other.

The invention claimed is:

1. A pants-type disposable diaper cover in combination with a removable absorptive pad, the pants-type disposable diaper cover comprising:
a plurality of elastically extensible members arranged between two nonwoven-fabric sheets, a waist opening and a pair of right and left leg openings being formed when the diaper cover is folded at a diaper crotch portion and when a front and a back are joined at edges thereof at two body side portions;
on an inner side of the pants-type disposable diaper cover, a pad-fixing sheet which is formed from a woven fabric, nonwoven fabric, or plastic film, and that has a front end portion fixed to the front of the diaper cover, a back end portion fixed to the back of the diaper cover, and a middle portion that is not fixed to the diaper cover so as to traverse the crotch portion and extend from the front to the back of the diaper cover, and that is arranged in a region of the diaper cover corresponding to a position for mounting said absorptive pad; and
said plurality of elastically extensible members including at least an elastically extensible waist member arranged around said waist opening and disposed on the front and back of the diaper cover;
a plurality of elastically extensible hip members arranged horizontally and spaced vertically from one another along the front and back of the diaper cover; and
a plurality of curved elastically extensible members arranged so as to extend in the front and in the back and from the body side portions to the crotch portion and so as to trace a trajectory extending from the crotch portion to the body side portions after traversing the position where said pad-fixing sheet is arranged on the crotch portion without forming any portion of or extension from said pad-fixing sheet so as to effect holding of said pad-fixing sheet between the front end portion and the back end portion of the diaper cover and holding of said pad-fixing sheet and absorptive pad against a wearer when the diaper cover is worn, wherein
the front end portion of the pad-fixing sheet is fixed in the region where the elastically extensible hip members of the front are arranged, and the back end portion of the pad-fixing sheet is fixed in the region where the elastically extensible hip members of the back are arranged, and beginning and terminal ends of the said curved elastically extensible members are connected so as to extend over a range of from substantially the top to the bottom of the front and back at said joined edges thereof and the bottommost of the curved elastically extensible members in the front and back, respectively, are disposed in close proximity to one another without mutually crossing one another at the crotch portion.

2. A pants-type disposable diaper cover as set forth in claim 1, wherein said absorptive pad is joined to said pad-fixing sheet by either a self-adhesive applied to a back of the absorptive pad or face fasteners disposed on said absorptive pad and said pad-fixing sheet.

3. A pants-type disposable diaper cover as set forth in claim 1, wherein said curved elastically extensible members are arranged through a spacing without intersecting each other.

4. A pants-type disposable diaper cover as set forth in claim 1, wherein the curved elastically extensible members arranged in said front and back cross in the transverse portion of the crotch side in arcuate curve shapes bulging to the crotch side.

5. A pants-type disposable diaper cover as set forth in claim 1, wherein the curved elastically extensible members arranged in said back are directionally turned back in the crossing portion on the crotch side to sides of the waist opening so as to trace a trajectory bulging to the sides of the waist opening at a substantially widthwise center and are then turned back again so that they cross in a trajectory substantially forming a W shape.

* * * * *